United States Patent
Manuel et al.

(10) Patent No.: US 9,629,873 B2
(45) Date of Patent: Apr. 25, 2017

(54) BIORESORBABLE METAL ALLOY AND IMPLANTS MADE OF SAME

(75) Inventors: Michele Viola Manuel, Gainsville, FL (US); Harpreet Singh Brar, Hillsboro, OR (US); Ida Svensson Berglund, Gainesville, FL (US); Benjamin George Keselowsky, Gainesville, FL (US); Malisa Sarntinoranont, Gainesville, FL (US)

(73) Assignee: UNIVERSITY OF FLORIDA RESEARCH FOUNDATION, INC., Gainvesville, FL (US)

(*) Notice: Subject to any disclaimer, the term of this patent is extended or adjusted under 35 U.S.C. 154(b) by 451 days.

(21) Appl. No.: 13/808,037

(22) PCT Filed: Jul. 2, 2011

(86) PCT No.: PCT/US2011/042892
§ 371 (c)(1),
(2), (4) Date: Jun. 7, 2013

(87) PCT Pub. No.: WO2012/003502
PCT Pub. Date: Jan. 5, 2012

(65) Prior Publication Data
US 2014/0154341 A1 Jun. 5, 2014

Related U.S. Application Data

(60) Provisional application No. 61/361,327, filed on Jul. 2, 2010.

(51) Int. Cl.
*A61K 33/06* (2006.01)
*C22C 23/00* (2006.01)
*A61L 27/04* (2006.01)
*A61L 27/58* (2006.01)

(52) U.S. Cl.
CPC ............ *A61K 33/06* (2013.01); *A61L 27/047* (2013.01); *A61L 27/58* (2013.01); *C22C 23/00* (2013.01)

(58) Field of Classification Search
CPC .............................. A61K 33/06; C22C 23/00
USPC .......................................... 420/402; 424/682
See application file for complete search history.

(56) References Cited

U.S. PATENT DOCUMENTS

| | | | |
|---|---|---|---|
| 6,896,517 B1 | 5/2005 | Bjoern | |
| 7,771,774 B2 | 8/2010 | Berckmans, III | |
| 2003/0087197 A1 | 5/2003 | Schulman | |
| 2004/0241314 A1 | 12/2004 | Li | |
| 2005/0079200 A1* | 4/2005 | Rathenow et al. | 424/423 |
| 2005/0250073 A1 | 11/2005 | Tresser | |
| 2005/0266041 A1 | 12/2005 | Gerold et al. | |
| 2006/0198869 A1 | 9/2006 | Furst et al. | |
| 2008/0243242 A1 | 10/2008 | Kappelt | |
| 2008/0312736 A1 | 12/2008 | Mueller | |
| 2009/0131540 A1 | 5/2009 | Hiromoto | |
| 2009/0226857 A1 | 9/2009 | Grant | |
| 2010/0075162 A1* | 3/2010 | Yang et al. | 428/457 |
| 2010/0161031 A1 | 6/2010 | Papirov et al. | |
| 2011/0054629 A1 | 3/2011 | Seok et al. | |
| 2011/0076319 A1 | 3/2011 | Orlowski et al. | |
| 2011/0319986 A1 | 12/2011 | Bayer | |

FOREIGN PATENT DOCUMENTS

| | | |
|---|---|---|
| EP | 0261470 A1 | 3/1988 |
| EP | 0263274 B1 | 4/1988 |
| EP | 2014319 A1 | 1/2009 |
| EP | 2022443 B1 | 2/2009 |
| EP | 2119414 B1 | 11/2009 |
| KR | 10-2008-0027202 A1 | 3/2008 |
| KR | 1020080027202 | * 3/2008 |
| KR | 10-2009-0099670 | 9/2009 |
| KR | 1020090099670 | * 9/2009 |
| WO | WO2006096720 A1 | 9/2006 |
| WO | WO2011105685 A2 | 9/2011 |

OTHER PUBLICATIONS

Brar, H. S. et al. "A study of biodegradable Mg-3Sc-3Y alloy and the effect of surface passivation on in-vitro degradation" Acta Biomaterialia 9 (2013) 5331-5340.

Chen SL, Daniel S, Zhang F, Chang YA, Yan XY, Xie FY, Schmid-Fetzer R, Oates WA. "The PANDAT Software Package and its Applications" CALPHAD 2002; 26: (175-188).

International Preliminary Report on Patentability for Application No. PCT/US2011/042892 Filing Date Jul. 2, 2011; Issue Date Jan. 8, 2013 (6 pages).

International Search Report for Application No. PCT/US2011/042892 Filing Date Jul. 2, 2011; Mailing Date Mar. 20, 2012 (4 pages).

Li Z, Gu X, Lou S, Zheng Y. "The development of binary Mg—Ca alloys for use as biodegradable materials within bone" Biomaterials 2007; 29: (1329-1344).

Wan Y, Xiong G, Luo H, He F, Huang Y, Zhou X. "Preparation and characterization of a new biomedical magnesium-calcium alloy" Materials & Design 2008; 29: (2034-2037).

Written Opinion for Application No. PCT/US2011/042892 Filing Date Jul. 2, 2011; Mailing Date Mar. 20, 2012 (5 pages).

International Search Report for Application No. PCT/US2014/045364 Filing Date Jul. 3, 2014; Mailing Date Oct. 28, 2014 (6 pages).

(Continued)

*Primary Examiner* — Janet Epps-Smith
*Assistant Examiner* — Courtney Brown
(74) *Attorney, Agent, or Firm* — Thomas Horstemeyer, LLP

(57) ABSTRACT

Disclosed herein is a non-toxic, bioresorbable, magnesium based alloy for use in production of implants. Specifically exemplified herein are alloy embodiments useful for orthopedic implants. Also disclosed are alloy materials that incorporate magnesium, calcium and strontium.

14 Claims, 12 Drawing Sheets

(56) References Cited

OTHER PUBLICATIONS

Written Opinion for International Application No. PCT/US2014/045364 Filing Date Jul. 3, 2014; Mailing Date Oct. 28, 2014 (9 pages).
International Search Report for Application No. PCT/US2014/064065 Filing Date Nov. 5, 2014; Mailing Date Feb. 18, 2015 (8 pages).
Written Opinion for Application No. PCT/US2014/064065 Filing Date 05 Nov. 2014; Mailing Date 18 Feb. 2015 (5 pp.).
Ida S. Berglund, et al.; Synthesis and Characterization of Mg—Ca—Sr Alloys for Biodegradable Orthopedic Implant Applications; Society for Biomaterials; Jun. 12, 2012; pp. 1524-1534.
M. Bornapour, et al.; Biocompatibility and Biodegradability of Mg—Sr Alloys: The Formation of Sr-Substituted Hydroxyapatite; Acta Biomaterialia vol. 9 (2013); Aug. 5, 2012; pp. 5319-5330.
Brar, et al. "Investigation of the mechanical and degradation properties of Mg—Zn—Sr alloys for use as potential biodegradable implant materials." Journal of the Mechanical Behavior of Biomedical Materials 7 (2012) 87-95.

\* cited by examiner

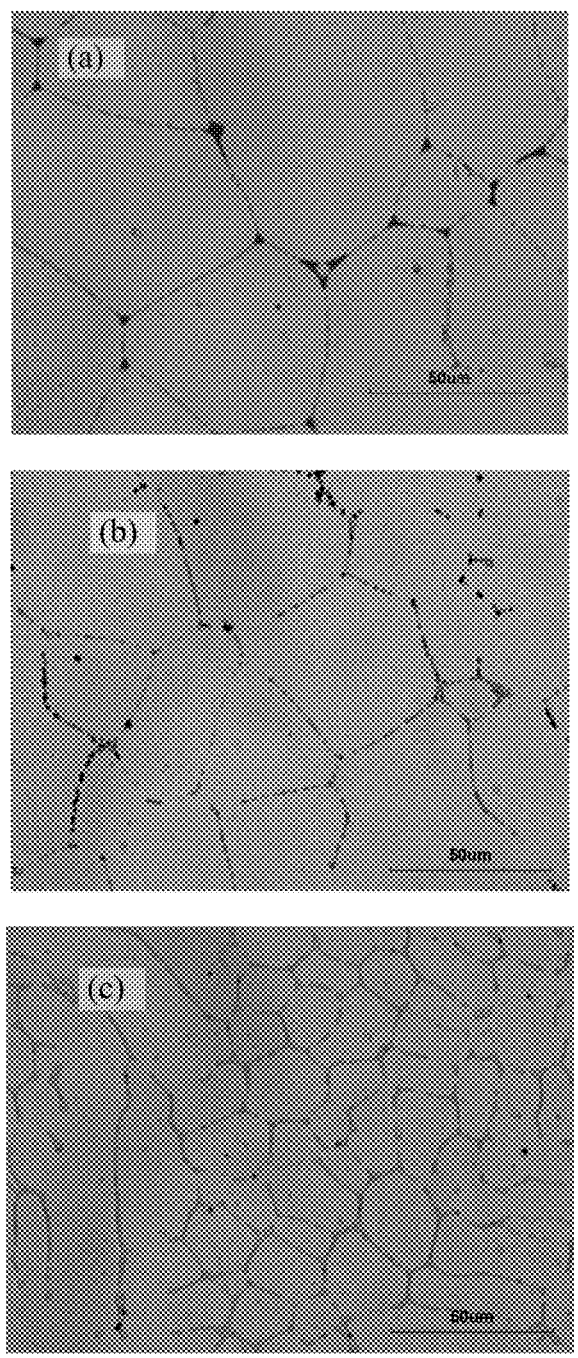
FIG. 10 Optical micrographs of solution treated alloys (1) Mg-0.5Sr (b) Mg-1.0Sr (c) Mg-1.5Sr

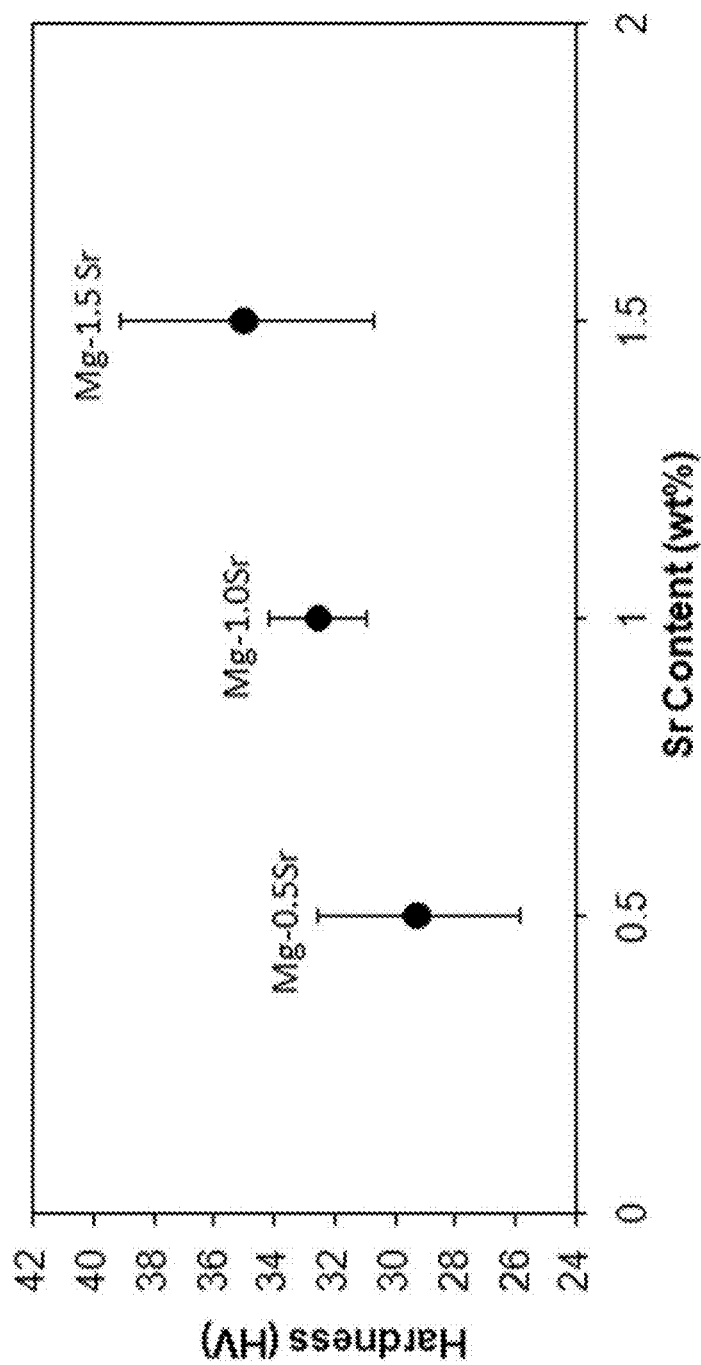
FIG. 11 Vickers microhardness of the binary Mg-Sr alloys

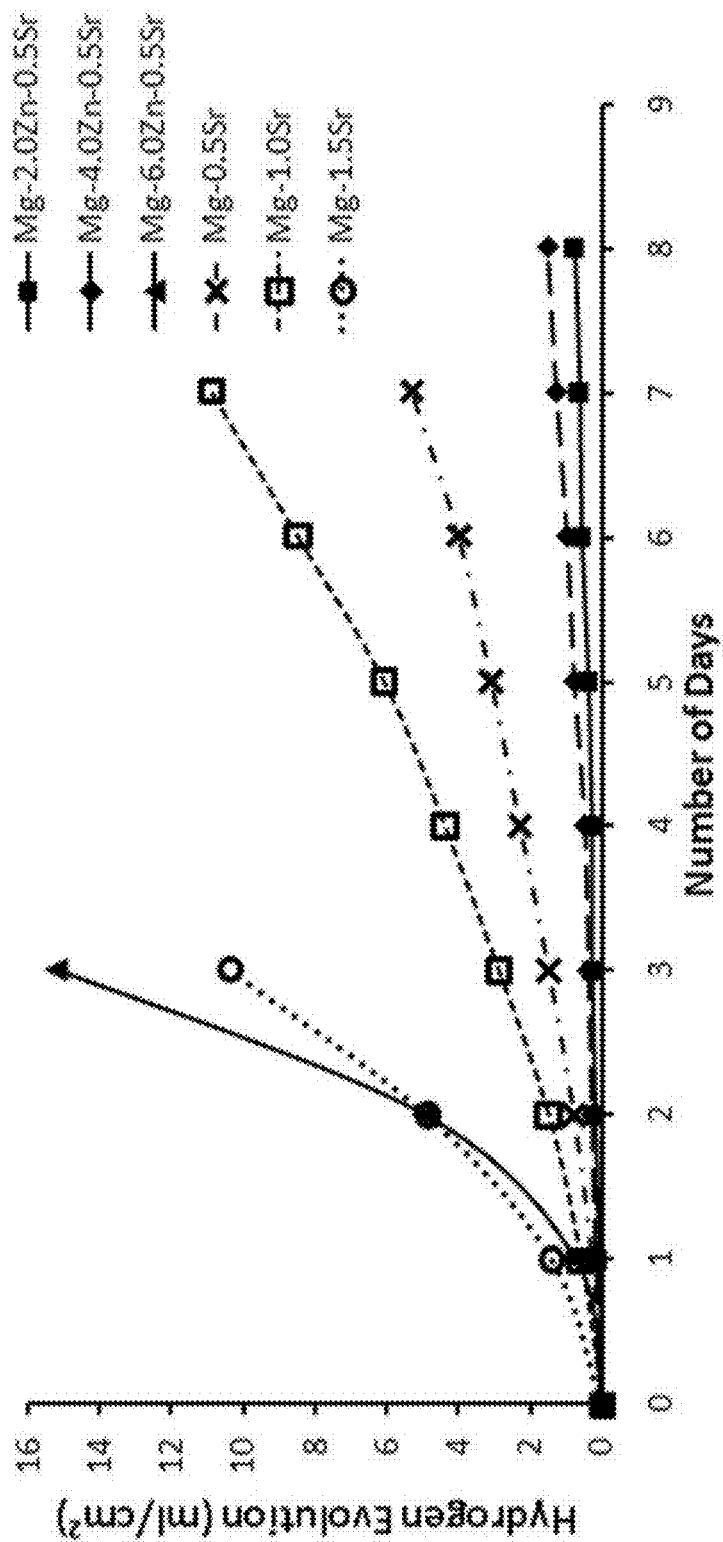
FIG. 12 Hydrogen evolution plot

BIORESORBABLE METAL ALLOY AND IMPLANTS MADE OF SAME

CROSS-REFERENCE TO RELATED APPLICATIONS

This application claims priority to U.S. Provisional Application No. 61/361,327 filed Jul. 2, 2010 and to International Application No. PCT/US2011/042892 filed on Jul. 2, 2011, the entire contents of which are incorporated herein in their entirety.

BACKGROUND OF THE INVENTION

Biomaterials are used in numerous medical applications today, such as fixation devices, replacements and surgical equipment. Implants are typical examples of a biomaterial application and there are several different implant materials used today. Many of these are however designed to stay in the body permanently even though they only serve their function temporarily. Even if the materials are biocompatible there are several complications associated with long term presence of implants, including allergy and sensitization. Many of these implants are only left in the body to eliminate risks concerning the removal process. Removing an implant usually involves surgery which increases both cost and patient morbidity. These negative consequences would be eliminated by using a biodegradable material. A completely biodegradable implant would dissolve and be absorbed by the body after the healing process is completed. Commonly used metallic implant materials include stainless steels, titanium alloys and cobalt-chromium alloys. These materials have great mechanical properties and are often used in load bearing applications. The mechanical properties of some common alloys can be seen in Table 1. However, many metallic corrosion products are harmful to the body and none of the implant metals used are biodegradable. Ceramic materials are known for their high strength and are generally biocompatible. Synthetic hydroxyapatite and other calcium phosphates as well as bioactive glass are commonly used materials for bone augmentation and bone replacement. They resemble the bone structure which gives good chemical bonding to bone and is therefore defined as bioactive. Alumina and zirconia are commonly used inert biomaterials. Ceramic coatings are frequently used on metallic implants to increase the biocompatibility and to induce bone ingrowth. The biggest disadvantage of ceramics is high brittleness, as can be seen in Table 1. There are numerous polymeric biomaterials used today, such as polyethylene (PE), polyvinylchloride (PVC), poly(methyl methacrylate) (PMMA) etcetera. However, all polymers have the disadvantage of low strength which eliminates their possibility to be used in load bearing applications, such as for example bone fixation devices.

TABLE 1

Mechanical properties of magnesium, human bone and some commonly used biomaterials.

|  | Elastic modulus (GPa) | Density (g/cm$^3$) | Yield strength (MPa) | Tensile strength (MPa) |
|---|---|---|---|---|
| Magnesium | 45[1] | 1.74[1] | 70[2] | 176[2] |
| Human cortical bone | 5-23[3] | 1.8-2.0[3] | 106-224[4] (compressive) | 51-172[4] |
| Stainless steel | 190[5] | 8.0[3] | 300-1200[5] | 480-620[3] |
| TI6Al4V | 114[1] | 4.43[1] | 896[1] | 1000[1] |
| Alumina | 380[4] | 3.95[6] | 2260-2600[6] | 270[4] |
| Bioactive glass | 35[3] | — | — | 40-200[2,3] |
| Synthetic hydroxyapatite | 73-117[7] | 3.1[7] | 600[7] (compressive) | 0.7[7] |
| Biodegradable PGA | 12.8[8] | 1.5[9] | — | 339-394[9] |
| Biodegradable L-PLA | 1.2-3[4] | — | — | 28-48[4] |

The ranges of values are depending on testing conditions or anatomical location.
References are compiled from different sources;
[1](ASM-International 1999),
[2](Cardarelli 2008),
[3](Witte, Hort et al. 2008),
[4](Kutz 2002),
[5](Bartel, Davy et al. 2006),
[6](Harper 2001),
[7](Staiger, Pietak et al. 2006),
[8](Maurus and Kaeding 2004),
[9](Brandrup, Immergut et al. 2005).

SUMMARY OF THE INVENTION

There is no material used today that has the strength of a metal or ceramic material as well as biodegradable properties. Magnesium is potentially an excellent implant material due to its attractive mechanical properties and non-toxicity. It has a high corrosion rate, especially in chloride containing solutions, which means that it will degrade in the human body. If the corrosion rate can be controlled the material is a great candidate for use as a biodegradable implant.

Magnesium alloys currently under investigation by researchers in the field for biomedical applications were originally designed for automotive and aerospace components with little consideration for their biocompatibility. As a result, most of the alloys currently being investigated contain toxic alloying elements. The inventors have sought to make a degradable implant material selecting the alloying elements for purposes of obtaining optimal mechanical functionality while maintaining biocompatibility. Calcium is an essential element for the human body and is non-toxic. Strontium is present in human bones and has been shown to promote osteoblast function and increase bone formation when added to hydroxyapatite, as compared to pure hydroxyapatite. This creates the opportunity to develop metals that can completely dissolve within the body and that release dissolution products that are 100% biocompatible and enhance the biological processes in bone. In addition to their biological response, calcium and strontium are known to strengthen magnesium alloys while increasing their corrosion resistance. Controlling these elements and the corresponding microstructures that develop upon processing, our magnesium-based alloy can be designed with controllable degradation rates and mechanical properties. Hence, the inventors have shown that the magnesium-based alloy system containing calcium and strontium will produce promising results.

Based on the research of inventors, it has been realized that magnesium alloys can be used in biomedical implant materials which will be advantageous over other materials as they can dissolve completely in the human body, while exhibiting the other desirous attributes of metal materials.

The development of the alloy embodiments, has now enabled the development of medical devices that do not need additional surgeries for their removal. This greatly reduces the cost of treatment and patient morbidity. A magnesium-based alloy containing calcium and strontium is an improvement over other magnesium alloy systems being investigated as both calcium and strontium are elements present in bones and are biocompatible whereas the alloying elements being used in other studies are toxic. Thus, using magnesium alloy containing calcium and strontium greatly reduces the risk of potential toxicity by the degradation products being released from the medical device.

BRIEF DESCRIPTION OF THE DRAWINGS

The advantages of this invention will be apparent upon consideration of the following detailed disclosure of the invention, especially when taken in conjunction with the accompanying drawings wherein:

FIG. 10: Optical micrographs of solution treated alloys (a) Mg-0.5Sr (b) Mg-1.0Sr (c) Mg-1.5Sr FIG. 11: Vickers microhardness of the binary Mg—Sr alloys FIG. 12: Hydrogen evolution plot

DETAILED DESCRIPTION

Figure 1:
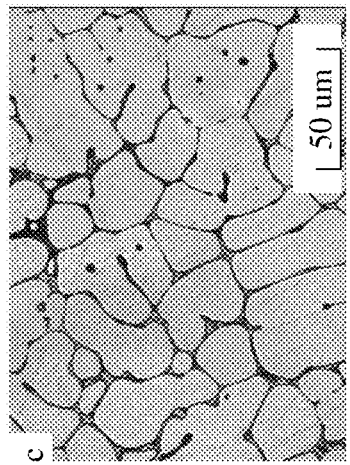
FIG. 1. Optical micrographs of a) Mg-0.5Ca-0.5Sr alloy, b) Mg-1.0Ca-0.5Sr alloy, c) Mg-1.0Ca-1.0Sr alloy, d) Mg-1.0Ca-2.0Sr alloy, and e) Mg-7.0Ca-3.5Sr alloy samples. The alloys show the characteristic dendritic structure associated with as-cast alloys. The darker regions are the Ca and Sr rich dendrites whereas the light regions are α-Mg regions.
Figure 1:
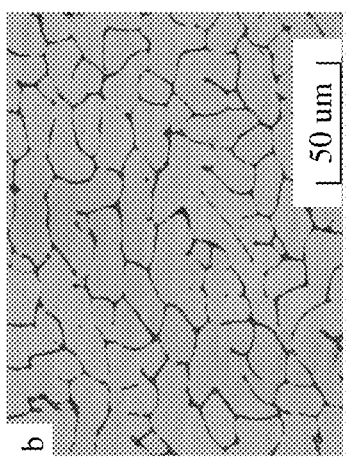
Figure 1:
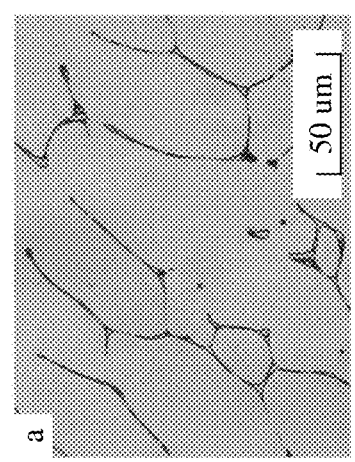
Figure 1:
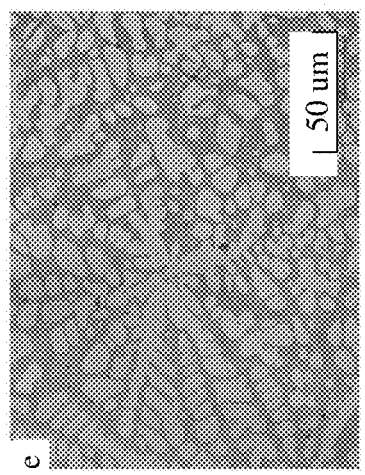
Figure 1:
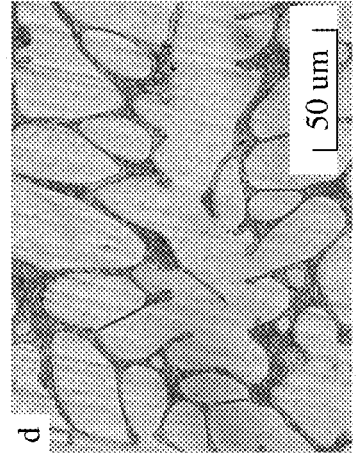

According to certain embodiments, the invention relates to a bioresorbable, non-toxic, osteogenic magnesium alloy. The alloy may include, by weight percentage, 0.3 to 10 percent calcium; 0.3 to 10 percent strontium; and 50 to 99.5 percent magnesium. In an exemplary embodiment, the alloy comprises 0.7 to 8 percent strontium. In a more specific embodiment, the alloy comprises 1 to 5 percent strontium. As used herein, the term osteogenic relates to the property of facilitating in growth of bone (osteoconductivity) and/or promoting new bone growth (osteoinductivity).

According to another embodiment, the invention pertains to a non-toxic, non-immunoreactive orthopedic implant comprised of a magnesium alloy that comprises calcium and strontium. The implant may be a composite where only a portion includes the magnesium alloy. In a more specific embodiment, the alloy comprises at least 50 percent total weight of the implant. There are numerous configurations that the implant may take for use in orthopedic type surgeries, including but not limited to, a spinal cage, a dowel, a wedge, a rod, a plate, a screw, a pin or a plate.

In alternative embodiment, the invention relates to an alloy that comprises magnesium, calcium and strontium and which is substantially free from aluminum, manganese, zirconium and/or zinc. As used herein, the term "substantially free" means that the element or compound comprises less than 3 percent by weight of the alloy.

In yet another embodiment, a biomaterial is disclosed which comprises a magnesium alloy at least 50% by weight. A biomaterial comprising a magnesium alloy at least 50% by weight includes a biomaterial which comprises a magnesium alloy at least 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% by weight, or a magnesium alloy 100% by weight.

According to another embodiment, the invention provides an implant to be positioned in vivo during surgery, especially orthopedic surgery to replace a joint, such as, for example, a knee joint or a hip joint. Thus, the implant can be used in a method for orthopedic surgery that includes surgically positioning the implant within a vertebrate in need thereof. If bone growth is facilitated, the implant can be termed part of an osteoconductive process that includes contacting a bone under in vivo conditions with the implant.

According to another embodiment, a magnesium alloy embodiment is used to coat an orthopedic or dental implant.

According to further embodiment, a dental implant embodiment is comprised of, at least partially, a magnesium alloy as taught herein.

EXAMPLES

Example 1

Alloy Preparation

In this study, five different Mg—Ca—Sr alloys with targeted compositions of Mg-0.5Ca-0.5Sr, Mg-1.0Ca-0.5Sr, Mg-1.0Ca-1.0Sr, Mg-1.0Ca-2.0Sr and Mg-7.0Ca-3.5Sr were prepared using high purity Mg chips (99.98%, Sigma-Aldrich, St. Louis, Mo.), Ca granules (99.5%, Alfa-Aesar, Ward Hill, Mass.) and Sr granules (99%, Sigma-Aldrich, St. Louis, Mo.). Melting of the alloys was carried out between 725-825° C. in high purity graphite crucibles. Each melt was held for approximately 40 min and stirred prior to pouring. The melt was then poured into high purity graphite moulds that were allowed to air-cool to room temperature. A protective argon atmosphere was maintained throughout the melting and casting process. The compositions of the as cast alloys were determined using inductively coupled plasma-atomic emission spectrometry (ICP-AES). The nominal and actual compositions of the investigated Mg alloys are listed in Table 2

Example 2

Microstructural Characterization

For microscopic evaluation, the samples were ground with silicon carbide (SiC) emery papers to 4000 grit, and polished to 0.3 micron using a colloidal silica suspension. The polished samples were etched using acetic picral as an etchant. The microstructural analysis was performed using light optic microscopy (LOM, Olympus PME3) and scanning electron microscopy (SEM, JEOL JSM 6400). Energy-dispersive X-ray spectroscopy (EDS, JEOL JSM 6400) and XRD (Phillips APD 3720) was employed to identify the different phases present in the alloys and the corroded surfaces.

Example 3

Immersion Tests

The samples were ground to 320 grit using SiC emery paper and then cleaned with ethanol. The immersion test was carried out at 37° C. in Hanks balanced salt solution containing 0.185 g/l $CaCl_2.2H_2O$, 0.40 g/l KCl, 0.06 g/l $KH_2PO_4$, 0.10 g/l $MgCl_2.6H_2O$, 0.10 g/l $MgSO_4.7H_2O$, 8.00 g/l NaCl, 0.35 g/l $NaHCO_3$, 0.48 g/l $Na_2HPO_4$, 1.0 g/l D-Glucose (Thermo Scientific Inc., Waltham, Mass.). The ratio of Hanks solution to the surface area of the samples was kept approximately 150. The high value was chosen to minimize the change in pH value during the experiment. The hydrogen evolution was measured by placing the samples at the bottom of a beaker with a funnel and a measuring cylinder placed on top of the beaker to collect and measure the volume of hydrogen gas evolved. The gas volume was measured every 24 h up to 8 days. The tests were performed in triplicates and the average of the data is reported.

Example 4

Compression Test

Compression testing of the alloys was carried out with an Instron 5582 universal testing machine. The compression samples were machined from as cast cylindrical rods. Each sample had a diameter of 6 mm and length of 9 mm. Compression tests were performed at a constant compression strain rate of 1% per min. Three compression samples were tested for each composition and the mean of the values are reported in Table 4.

Example 5

Cytotoxicity Evaluation

Toxicity testing was carried out on alloy extracts. Alloy samples were polished using 4000 grit paper and then sterilized by rinsing in ethanol and incubating under ultraviolet light for 15 min. The samples were put in a 50 ml conical tube and incubated in 1 ml of culture media per cm2 of metal surface area, for 72 h at 37° C. in a humidified atmosphere of 5% CO2 in air. The culture media consisted of α-minimal essential medium (α-MEM) supplemented with 10% fetal bovine serum, 1% L-glutamine, 1% pyruvate and 1% penicillin/streptomycin (Thermo Scientific Inc., Waltham, Mass.). After 72 h, alloy samples were removed from the conical tube and the alloy extracts were filtered through a 0.22 μm pore size filter and then serially diluted to make 50% and 10% concentrates with the fresh culture media. The diluted extraction media were refrigerated at 4° C. until utilized. The composition of the dissolved ions in the culture media and alloy extracts was measured using ICP. X-ray Diffraction was employed for characterization of the degradation products on the surface of the samples after immersion.

MC3T3-E1 mouse osteoblastic cell line was utilized for experiments and cells were cultured in a-MEM differentiation media using standard procedures. The control groups used untreated cells in culture media as the negative control and cells treated with 1% triton X-100 in culture media as the positive control. Cells were incubated in 24-well polystyrene plates at a density of 1×106 cells per well and incubated for 24 h to allow attachment. The media was then replaced with 1 ml of extraction media per well. The LDH cytotoxicity detection assay (Roche Applied Sciences) was performed on the extraction media as per the manufacturer's protocol at 3 and 5 days of culture and measured spectrophotometrically at 490 nm (Victor 3 and Wallac 1420, PerkinElmer, Waltham, Mass.). The supernatant was replaced with fresh extraction media on the end of day 3 upon collection of the extraction media. The medium pH was not adjusted during the tests. Statistical analyses were performed using general linear nested model ANOVA with Systat statistical software (Version 12, Systat Software, San Jose, Calif.) and significant differences were obtained using Tukey's honestly significant difference test. The data was pooled from 3 different experiments with n of ≥9.

The following examples relate to Examples 1-5 above

Example 6

Alloy Microstructural Characterization

Figure 2:
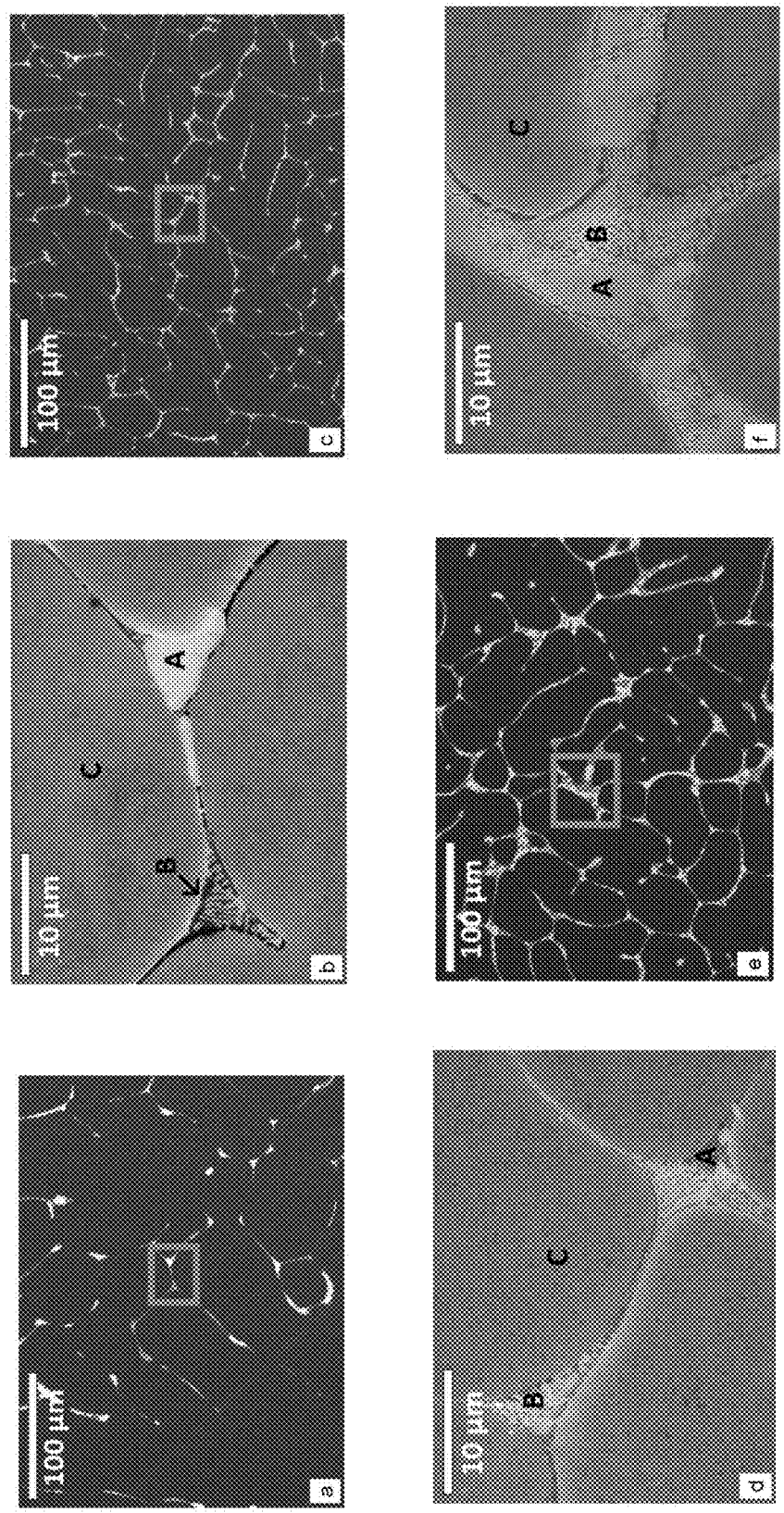
FIG. 2. SEM images of a-b) Mg-0.5Ca-0.5Sr alloy, c-d) Mg-1.0Ca-0.5Sr alloy, and e-f) Mg-1.0Ca-1.0Sr alloy. The (b), (d) and (f) pictures show the magnified images of the area in the squares and identify the phases present. Phase A is $Mg_{17}Sr_2$, Phase B is the $Mg_2Ca$ present in the eutectic and Phase C is the α-Mg phase.
Figure 3:
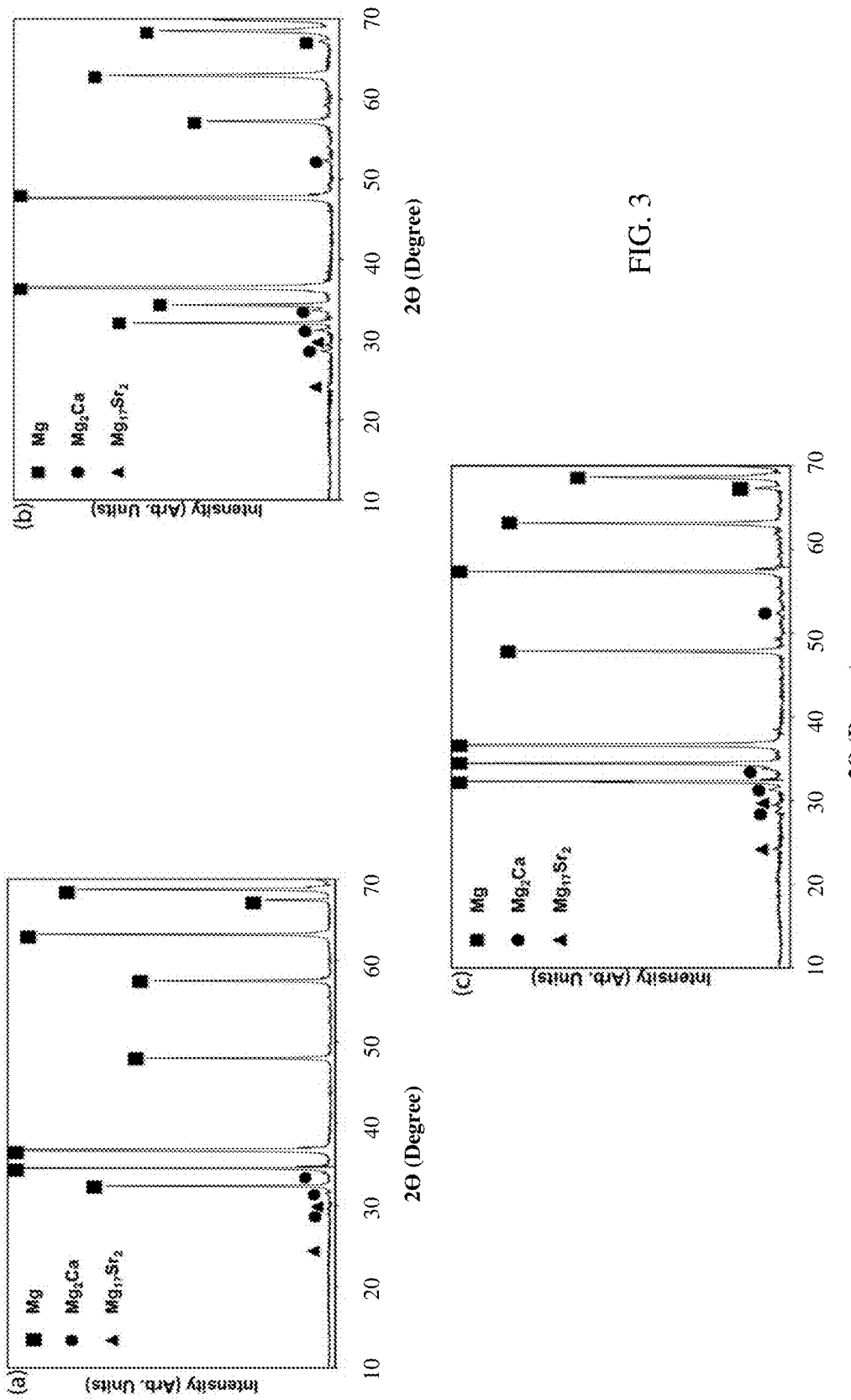
FIG. 3. XRD patterns of a) Mg-0.5Ca-0.5Sr alloy, b) Mg-1.0Ca-0.5Sr alloy, and c) Mg-1.0Ca-1.0Sr alloy samples. All three alloys display the same phases: α-Mg, $Mg_2Ca$ and $Mg_{17}Sr_2$.

FIG. 1 shows the optical micrographs of the five alloys. All alloys morphologically display large irregular, ellipsoidal-shaped α-Mg phase dendrites and intermetallic compounds in the interdendritic regions. Except Mg-0.5Ca-0.5Sr, all of the alloys have a continuous precipitate and eutectic network along the dendrites. Since Mg-7.0Ca-3.5Sr and Mg-1.0Ca-2.0Sr showed low corrosion resistance and dissolved quickly (see next section), thus they were excluded from any further microstructural analysis. FIG. 2 shows the SEM images of the microstructure of Mg-0.5Ca-0.5Sr, Mg-1.0Ca-0.5Sr, and Mg-1.0Ca-1.0Sr alloys. It can be seen that the dendrite spacing of Mg-0.5Ca-0.5Sr is relatively larger than that of Mg-1.0Ca-0.5Sr and Mg-1.0Ca-1.0Sr. It can be seen that with an increase in Ca and Sr contents, the amount of intermetallic compounds along the dendrite boundaries increases. Quantitative analysis was performed using EDS to determine the approximate composition of the different phases (labeled A, B and C) in FIG. 2 and the results are summarized in Table 3. These intermetallic compounds were identified as $Mg_2Ca$ and $Mg_{17}Sr_2$ using XRD and the XRD patterns are shown in FIG. 3. It can be seen that though the amount of secondary phases present in the alloys is different, all of the alloys have the same phases present.

Example 7

Immersion Test

Figure 4:
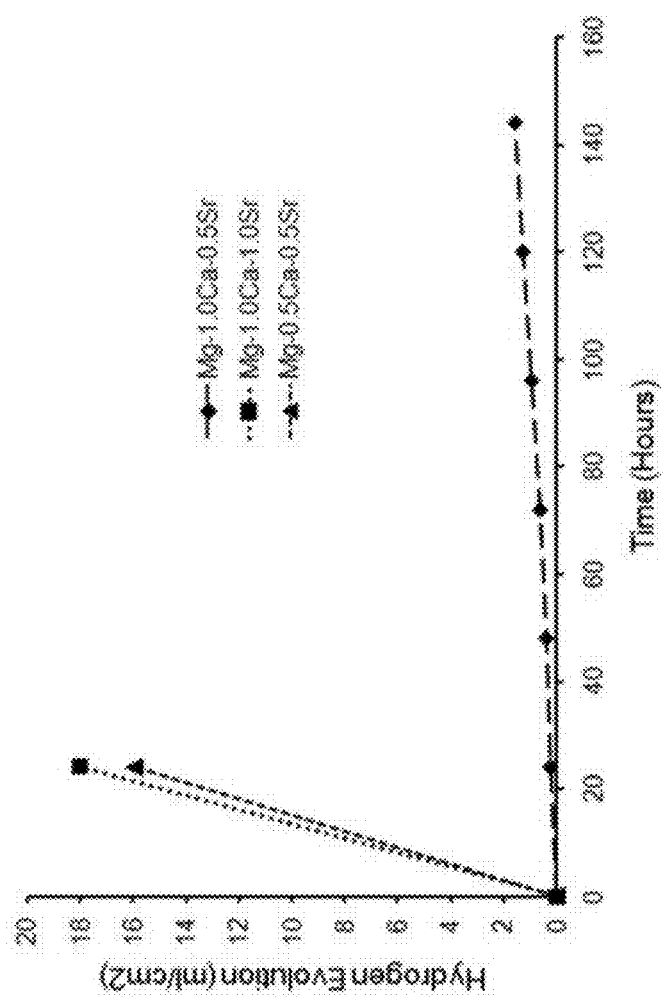
FIG. 4. Hydrogen evolution volumes of alloys immersed in Hank's solution. High purity Mg (99.95%) is shown for comparison.
Figure 5:
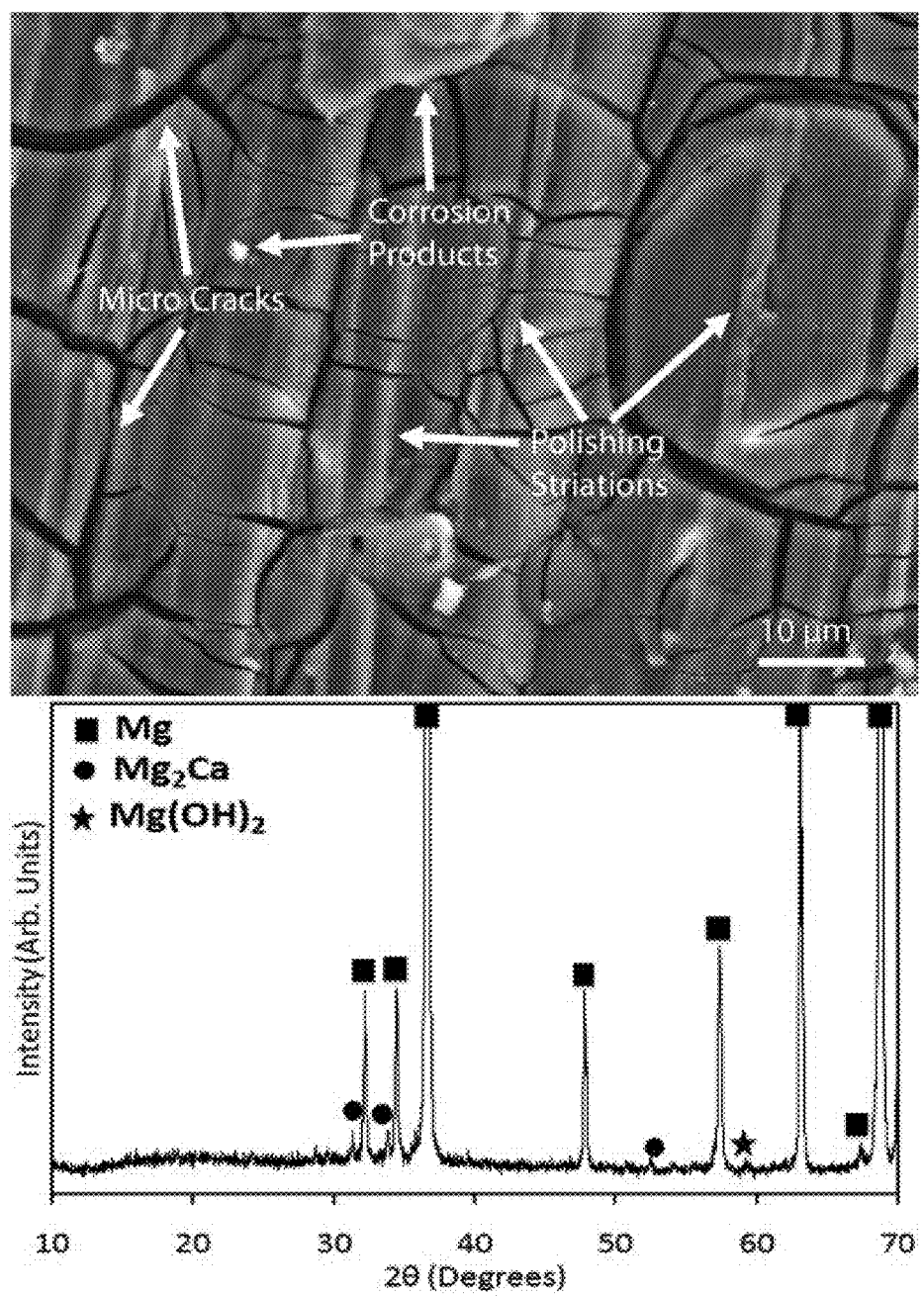
FIG. 5. SEM image and XRD pattern of the corroded surface of Mg-1.0Ca-0.5Sr alloy. The large striations on the surface of the samples are due to polishing effects during sample preparation. The microcracks, striations and corrosion products are labelled accordingly. It is apparent in this figure there is a significant number of microcracks forming on the sample surface.

The results of the hydrogen evolution test can be seen in FIG. 4. The alloys with high amounts of alloying additions, Mg-7.0Ca-3.5Sr and Mg-1.0Ca-2.0Sr, are not shown due to their rapid corrosion rate. These alloys completely dissolved and disintegrated within the first 24 h of immersion, thus surface area in contact with the Hanks solution could not be calculated. It can be seen that Mg-1.0Ca-1.0Sr and Mg-0.5Ca-0.5Sr alloys also show rapid degradation. The alloy with the slowest degradation rate was Mg-1.0Ca-0.5Sr. This alloy demonstrated a significantly lower hydrogen evolution of approximately 0.01 ml/cm$^2$/h. This is much lower than that of traditional Mg alloys like AZ91 and ZE41. It was also observed that the degradation was more rapid in the beginning, followed by stabilization of the corrosion rate. FIG. 5 shows the SEM image and XRD pattern of the corroded surface of Mg-1.0Ca-0.5Sr alloy after three days of immersion in culture media according to the extraction process mentioned under the toxicity test section. It can be observed that scratches from polishing are still visible, implying that there is no significant corrosion of the surface or minimal deposition of corrosion products on the surface.

Figure 6:
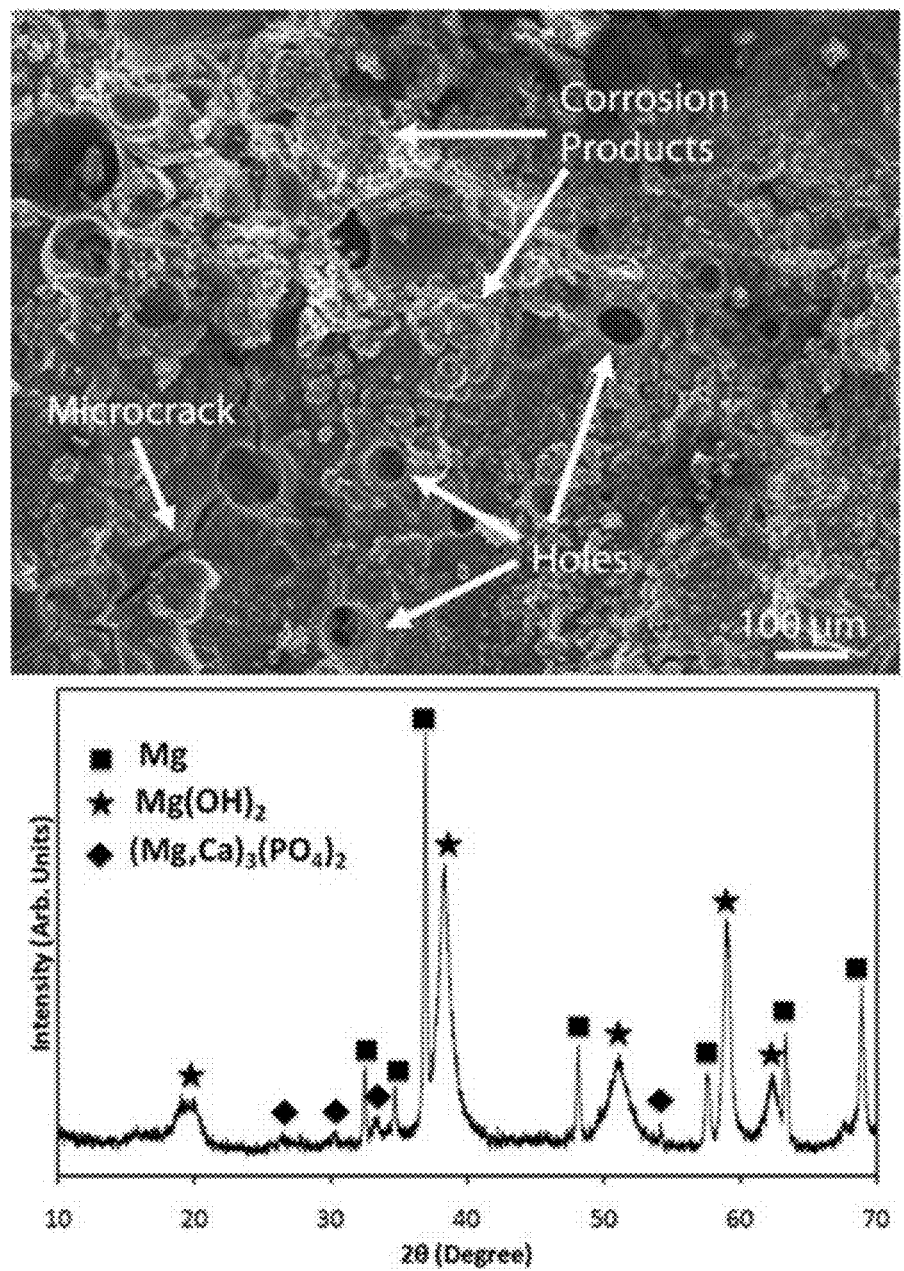
FIG. 6. SEM image and XRD pattern of the corroded surface of Mg-1.0Ca-1.0Sr alloy. The amount of corrosion products on the surface is significantly greater than that of Mg-1Ca-0.5Sr. The corrosion products, microcracks and holes in the surface layer are labeled. It can be seen that the holes run deep through the surface layer and can assist in the flow of media to unprotected surface beneath the corrosion layer. The XRD shows the presence of $Mg(OH)_2$ and $(Mg, Ca)_3(PO_4)_2$ phosphate on the surface of the corroded sample.

FIG. 6 shows the Mg-1.0Ca-1.0Sr alloy under similar conditions. Mg-0.5Ca-0.5Sr showed corrosion behavior similar to Mg-1.0Ca-1.0Sr and is hence not shown here. The SEM micrograph shows severe corrosion and significant deposition of corrosion products on the surface of the alloy. The XRD images in FIGS. 5 and 6 show that in both the alloys, $Mg(OH)_2$ is present on the surface of the degrading samples. For the Mg-1.0Ca-1.0Sr alloy sample, $(Mg,Ca)_3(PO_4)_2$ is also observed in the corrosion layer.

Example 8

Compression Test

Mechanical properties of the alloys are enumerated in Table 4. Compressive strength of Mg-0.5Ca-0.5Sr alloy and Mg-1.0Ca-0.5Sr alloy is similar whereas the strength of Mg-1.0Ca-1.0Sr alloy is much lower. The mechanical properties are similar to what have been reported for binary Mg—Ca alloys with similar amounts of Ca additions (Wan Y, Xiong G, Luo H, He F, Huang Y, Zhou X. Preparation and characterization of a new biomedical magnesium-calcium alloy. Materials & Design 2008; 29:2034-2037).

Example 9

Cytotoxicity Evaluation

Figure 7:
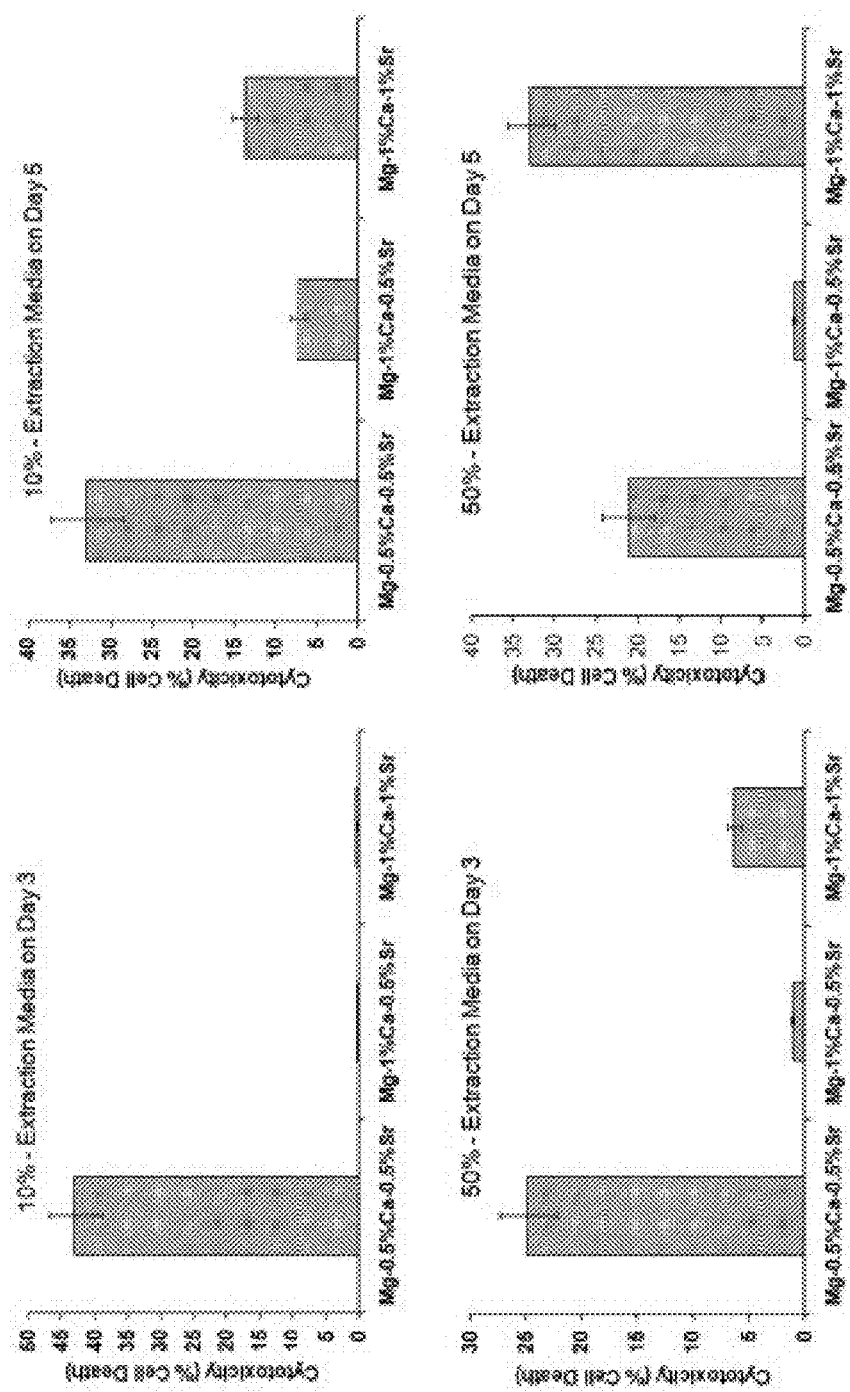
FIG. 7. Toxicity on MC3T3-E1 cells expressed as a percentage of dead cells for different alloys after culturing in 10% alloy extraction media on day 3, 10% alloy extraction media on day 5, 50% alloy extraction media on day 3, and 50% alloy extraction media on day 5.
Figure 8:
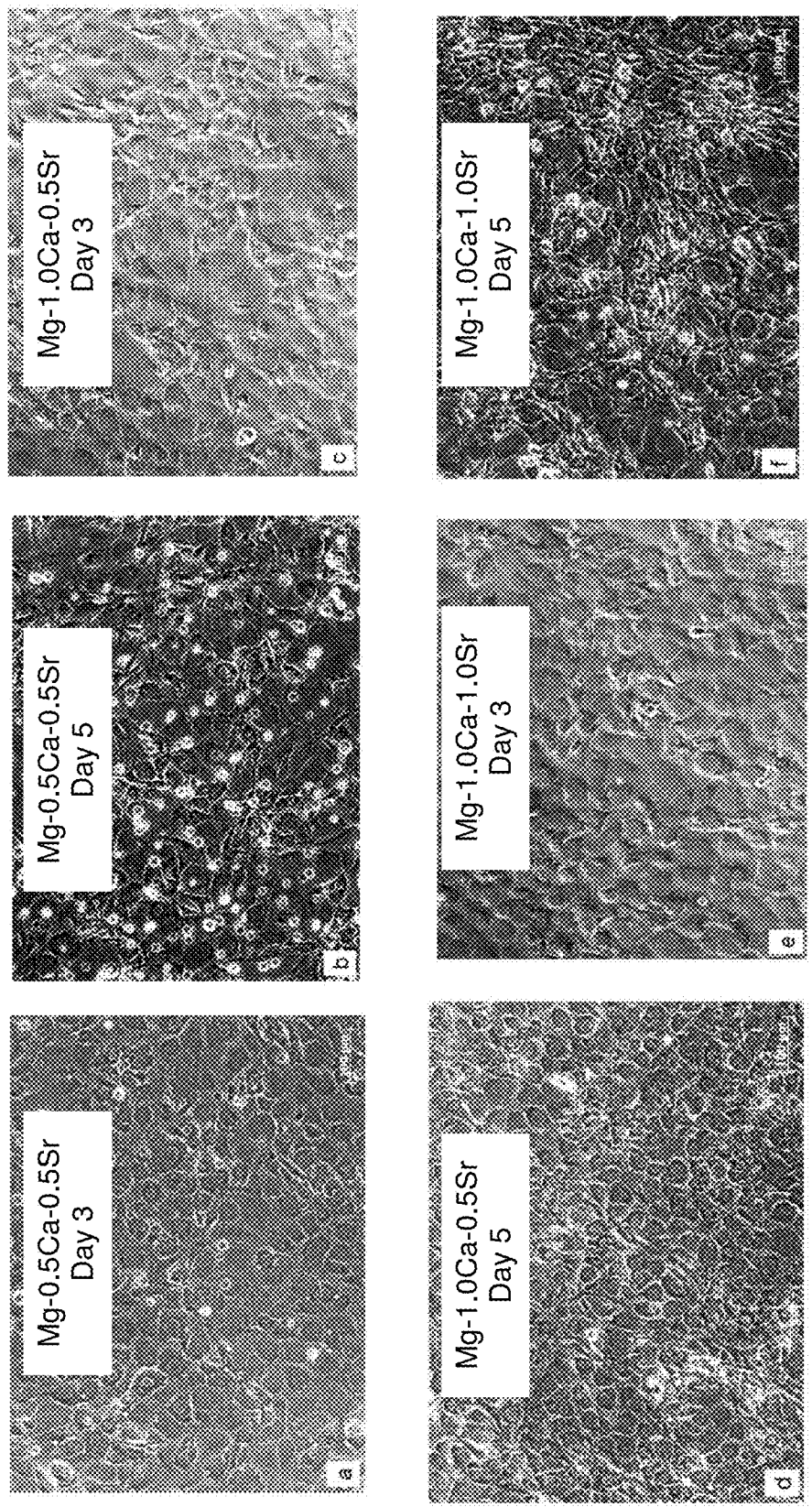
FIG. 8. Optical Morphologies of MC3T3-E1 cells cultured in 50% concentration of a-b) Mg-0.5Ca-0.5Sr c-d) Mg-1.0Ca-0.5Sr and e-f) Mg-1.0Ca-1.0Sr alloy extracts respectively, after 3 and 5 days of culturing.
Figure 9:
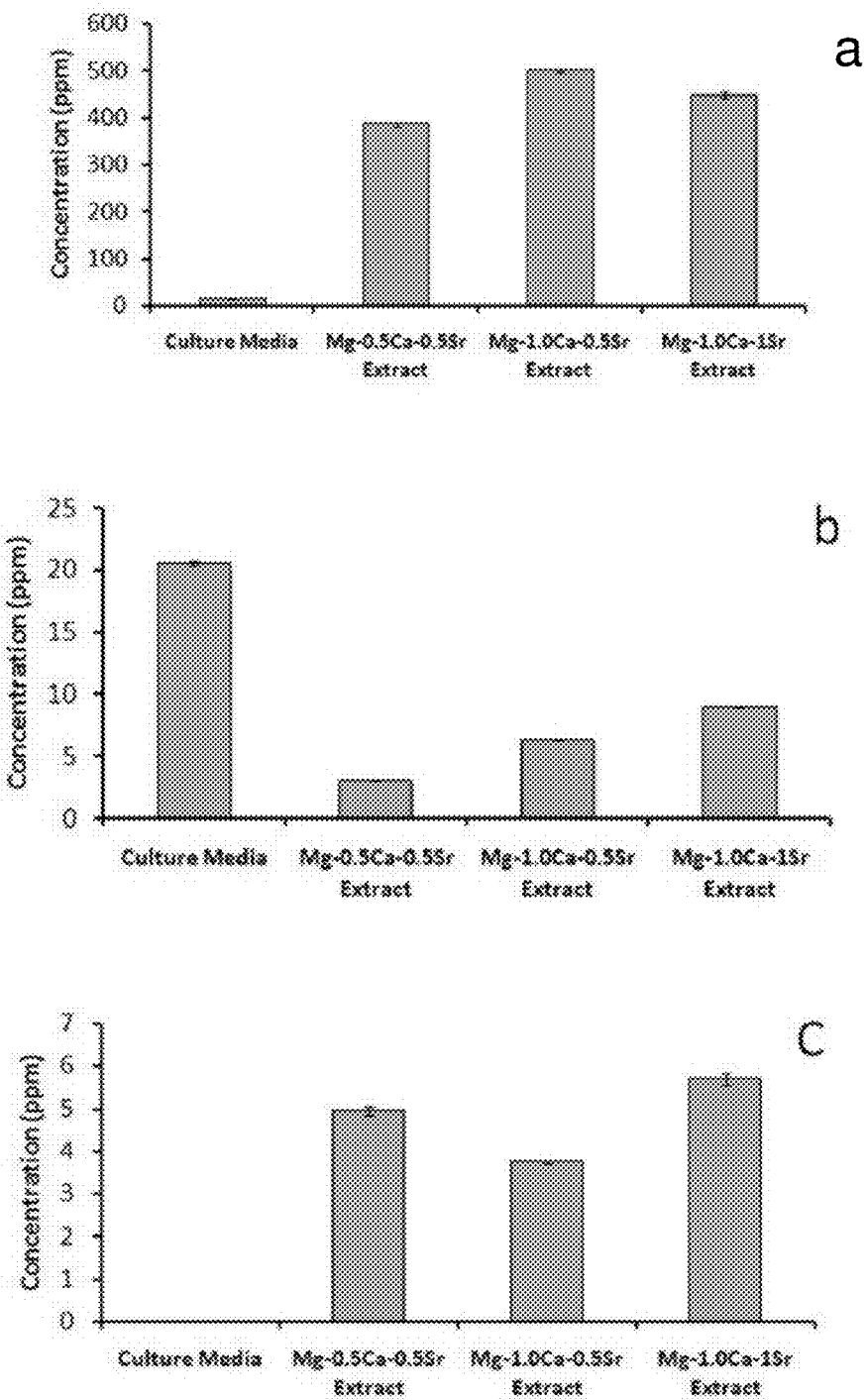
FIG. 9. Alloy extract ion concentrations of a) Mg, b) Ca and c) Sr. The columns show the average value of five measurements on each sample with error bars showing ±1 standard deviation.

FIG. 7(a-d) shows differential osteoblast cytotoxic response observed upon culture of these cells with varying concentrations of Mg, Ca and Sr at different days. The bar graphs represent the average cytotoxicity of the cells in terms of percentage dead cells relative to the control, with standard error against varying alloys and concentrates on different test days. It was observed that the cytotoxicity was the least for the Mg-1.0Ca-0.5Sr alloy for all days and at different percentages of extraction media. The Mg-0.5Ca-0.5.Sr alloy extracts showed the highest cytotoxicity for all days and concentrations except for the 50% concentrate on day 5 where Mg-1.0Ca-1.0Sr alloy demonstrated higher toxicity. FIG. 8 shows bright field images of the cells cultured with 50% extraction media at different days. The rounded/dead cells were found to be highest for the Mg-0.5Ca-0.5Sr alloy extract, shown in FIG. 8a-b, followed by the Mg-1.0Ca-1.0Sr alloy extract, shown in FIG. 8e-f. The Mg-1.0Ca-0.5Sr alloy extract, FIG. 8c-d, resulted in the least number of rounded/dead cells. The micrographs obtained via bright field imaging support the cytotoxicity data observed using LDH assay. FIG. 9(a-c) shows the amount of $Mg^{2+}$, $Ca^{2+}$ and $Sr^{2+}$ ions present in the culture media and the alloy extracts. It is observed that all the extracts had a significantly high amount of $Mg^{2+}$ and $Sr^{2+}$ ions as compared to the media. However, the amount of $Ca^{2+}$ was lower than that present in the culture media.

Discussion Related to Examples 1-9

The study provided in Examples 1-9 found that the degradation rate of Mg-1.0Ca-0.5Sr alloy shows a significant improvement over that of Mg-1.0Ca binary alloy (Li Z, Gu X, Lou S, Zheng Y. The development of binary Mg—Ca alloys for use as biodegradable materials within bone. Biomaterials 2007; 29:1329-1344). The amount of hydrogen evolution is reduced by an order of magnitude as compared to results reported on cast Mg-1.0Ca alloy. This could be highly beneficial in prevention of subcutaneous gas bubbles around the implants, thereby providing a better healing environment.

There are likely two possible reasons for the improved corrosion resistance of Mg-1.0Ca-0.5Sr as compared to Mg-0.5Ca-0.5Sr and Mg-1.0Ca-1.0Sr alloys. First, the difference in the amount and nature of precipitates present and secondly, the variations in grain size influencing the degradation properties in these alloys. In the microstructures shown in FIG. 2, it can be observed that Mg-0.5Ca-0.5Sr and Mg-1.0Ca-1.0Sr contain higher amounts of the Sr-rich phase (marked A in the images) than Mg-1.0Ca-0.5Sr alloy. This observation is also in accordance with the phase fractions of different phases calculated using the PANDAT™ software system33 (CompuTherm LLC, Madison, Wis.) and a proprietary thermodynamic Mg database (PanMagnesium-Thermodynamic Database for commercial Magnesium Alloys. Version 7. Madison, Wis.: CompuTherm LLC; 2007). By using Gibbs energy minimization protocols, PANDAT is useful in calculating thermodynamic data such as phase equilibria and transformations. The presence of a higher amount of Sr-rich phase can possibly decrease the corrosion resistance of the alloy by providing an increased interface area for micro-galvanic coupling between different phases. As can be seen in the micrographs, the Mg-1.0Ca-0.5Sr alloy has significantly smaller grains than the other alloys. Overall, the enhanced corrosion resistance of Mg-1.0Ca-0.5Sr can most likely be attributed to the presence of a right balance of efficient precipitate distribution along grain boundaries and small grain size.

The formation of degradation products on the surface of the material also affects the subsequent degradation. As shown in the XRD plots in FIG. 5 and FIG. 6, $Mg(OH)_2$ is formed on the alloy surface during degradation. As the rate of hydrogen evolution for Mg-1.0Ca-0.5Sr decreases with increasing time, the $Mg(OH)_2$ layer formed on the surface seems to be protective in nature and growing with time. On the other hand, even though both $Mg(OH)_2$ and $(Mg,Ca)_3(PO4)_2$ was found on the surface of Mg-1.0Ca-1.0Sr, the degradation layer does not seem to be protective. As observed in the SEM images, large holes leading to subsurface tunnels exist in the outer layers of the alloy. These defects, which are caused by pitting corrosion, lead to highly localized attacks that promote the flow of the media to the unprotected alloy surface, resulting in high degradation rate even after formation of a thick degradation layer.

The above examples shows that Mg-0.5Ca-0.5Sr and Mg-1.0Ca-0.5Sr alloys have very similar mechanical properties, but with further increase in Sr and Ca content, the ultimate compression strength decreases. It has been previously reported that the mechanical properties degrade in binary Mg—Ca alloys when Ca content is increased above 1 wt % due to precipitation of Mg2Ca along grain boundaries. Adding 0.5 wt % Sr has a positive effect on the mechanical properties of Mg—Ca as the higher compressive strength is achieved as compared to binary Mg—Ca alloys with similar Ca content. However, addition of 1 wt % Sr reduces the compressive strength as compared to Mg-1.0Ca binary alloy (Wan Y, Xiong G, Luo H, He F, Huang Y, Zhou X. Preparation and characterization of a new biomedical magnesium-calcium alloy. Materials & Design 2008; 29:2034-2037). This can be attributed to the accumulation of greater amounts of eutectic and Sr-rich intermetallics on grain boundaries as seen in FIG. 2e, thereby increasing the brittleness and decreasing the compressive strength at failure. It should also be noted that even though the solubility of Ca in Mg is 0.8 wt % at room temperature, (Chen S L, Daniel S, Zhang F, Chang Y A, Yan X Y, Xie F Y, Schmid-Fetzer R, Oates W A. The PANDAT Software Package and its Applications. CALPHAD 2002; 26:175-188), EDS analysis of cast alloys did not show any Ca or Sr in the Mg matrix except in Mg-1.0Ca-1.0Sr alloy. Therefore, in low Ca and Sr containing cast alloys, the mechanical and electrochemical behavior of the alloys predominantly depends on the secondary phases along grain boundaries.

Upon evaluation of the ICP data detailing the concentration of ions in alloy extracts, it is apparent that the concentrations of $Mg^{2+}$ and $Sr^{2+}$ ions in the alloy extracts from the three alloys with the lowest degradation rate exceed the concentration of $Mg^{2+}$ and $Sr^{2+}$ ions in the as received culture media (note that there are no $Sr^{2+}$ ions present in the as-received culture media). Next, the concentration of $Ca^{2+}$ ions in the alloy extract is lower than in the as-received media. Inductively coupled plasma results coupled with the degradation rate and alloy composition indicate that the concentration of ions in the solution is potentially controlled by two different reaction mechanisms. The first reaction is the dissolution of ions from the alloys into the media due to corrosion while the second reaction is the formation of corrosion products from ions and their deposition on the surface. The increased amount of $Mg^{2+}$ and $Sr^{2+}$ ions as compared to culture media can be directly attributed to the dissolution of the alloys.

Even though Mg-1.0Ca-1.0Sr has the highest degradation rate and has the highest amount of phosphates present on the surface, it also has the highest amount of $Ca^{2+}$ among alloy extracts. This can most likely be attributed to the higher amount of $Ca^{2+}$ going into solution due to fast degradation. On the other hand, Mg-0.5Ca-0.5Sr has the least amount of $Ca^{2+}$ ions present as its Ca content is half of Mg-1.0Ca-1.0Sr, thereby releasing smaller amount of $Ca^{2+}$ ions into the solution. $Sr^{2+}$ ions follow the degradation rate, with Mg-1.0Ca-0.5Sr giving out least amount and Mg-1.0Ca-1.0Sr giving out the maximum amount of $Sr^{2+}$ ions.

The in-vitro cytotoxicity test results show that while the extracts from the Mg-0.5Ca-0.5Sr alloy induced approximately 45% cell death to MC3T3-E1 osteoblasts, the Mg-1.0Ca-0.5Sr alloy showed negligible or very low toxicity for both 50% and 10% extracts at both 3 days and 5 days. Furthermore, when comparing the cytotoxicity of all of the alloy extracts after 5 days to that after 3 days, no significant increase was observed. This demonstrates that there is no rapid increase in cytotoxicity with increase in interaction time with the cells. Interestingly, the cell death for the Mg-0.5Ca-0.5Sr extracts appear to decrease with time. It is unclear at this point if this is related to a decrease in the toxicity of the solution over time as ions may become sequestered, or possibly if released LDH may be unstable once released from lysed cells over the 5 day period.

Conclusions Drawn from Examples 1-9

In this study, Mg-based alloying system with Ca and Sr was investigated for its potential application as degradable orthopedic implant material. The alloys were mainly composed of three phases; α-Mg, $Mg_2Ca$ and $Mg_{17}Sr_2$, which control the mechanical properties and the biocorrosion behavior. The alloys were found to have better mechanical properties than binary Mg—Ca alloys with similar amount of Ca additions. It was found that low amounts of alloying elements enhance the corrosion properties in Hanks' solution, with the optimal composition of Mg-1.0Ca-0.5Sr. At higher concentrations, the degradation rate increases possibly due to formation of higher amount of secondary phases. It was shown that $Mg(OH)_2$ and $(Mg,Ca)_3(PO4)_2$ precipitated on the surface of the degrading material. Cytotoxicity tests on alloy components demonstrated that Mg-1.0Ca-0.5Sr resulted in almost negligible toxicity, and even the toxicity of Mg-0.5Ca-0.5Sr decreases with time. Collectively, the results conclude that the Mg—Ca—Sr system may be used for biodegradable orthopedic implant applications.

Example 10

Alloy Preparation

It the present study, three binary Mg-x wt % Sr (x=0.5, 1.0, 1.5) alloys and three ternary Mg-x wt % Zn-0.5 wt % Sr (x=2, 4, 6) alloys were prepared using Mg chips (99.98%, Sigma-Aldrich, St. Louis, Mo.), Sr granules (99.9%, Sigma-Aldrich, St. Louis, Mo.) and Zn granules (99.99%, Alfa-Aesar, Ward Hill, Mass.). The elements were mixed in desired proportions and heated at 850° C. in a graphite crucible. The melt was kept at this temperature for 45 minutes and stirred once using graphite rod. The melt was then poured into graphite mould that was kept at room temperature. The entire process of melting and casting was performed in a glove box under argon atmosphere to prevent oxidation.

Example 11

Heat Treatments and Age Hardening Response

The binary Mg—Sr were encapsulated in quartz tubes under vacuum for homogenization treatments. Mg—Sr alloys were homogenized at 450° C. for 18 hours and quenched in water. The microstructure of binary Mg—Sr alloys is shown in FIG. 10(a-c).

Vicker's microhardness testing was used to measure the hardness of the Mg—Sr alloys. The testing was performed using 300 gf load on the alloys for 15 seconds. All samples were polished to a 0.3 μm finish prior to testing to minimize the influence of surface defects in the analysis. The hardness of the alloys is shown in FIG. 11. It can be seen that the increase in Sr content increases the hardness of the alloys Example 12

Tensile Testing

Tensile testing was used to determine the yield strength (YS) and ultimate tensile strength (UTS) of the alloy samples. The alloys were cast into rectangular dog bone shaped samples using a graphite mould. The Mg—Sr tensile samples were homogenized at 450° C. before testing. The mechanical properties of the alloys is shown in Table 5.

Example 13

Dissolution Behavior

The amount of hydrogen evolution by the binary Mg—Sr and ternary alloys Mg—Zn—Sr in HBSS is shown in FIG. 12. Among Mg—Sr alloys, Mg-0.5Sr alloy had the lowest degradation rate. The degradation rate of the binary increased with increase in Sr content with the best performing alloy being Mg-0.5Sr.

In reviewing the detailed disclosure, and the specification more generally, it should be borne in mind that all patents, patent applications, patent publications, technical publications, scientific publications, and other references referenced herein are hereby incorporated by reference to the extent not inconsistent with the teachings herein.

It is important to an understanding of the present invention to note that all technical and scientific terms used herein, unless defined herein, are intended to have the same meaning as commonly understood by one of ordinary skill in the art. The techniques employed herein are also those that are known to one of ordinary skill in the art, unless stated otherwise. For purposes of more clearly facilitating an understanding the invention as disclosed and claimed herein, the following definitions are provided.

While a number of embodiments of the present invention have been shown and described herein in the present context, such embodiments are provided by way of example only, and not of limitation. Numerous variations, changes and substitutions will occur to those of skilled in the art without materially departing from the invention herein. For example, the present invention need not be limited to best mode disclosed herein, since other applications can equally benefit from the teachings of the present invention. Also, in the claims, means-plus-function and step-plus-function clauses are intended to cover the structures and acts, respectively, described herein as performing the recited function and not only structural equivalents or act equivalents, but also equivalent structures or equivalent acts, respectively. Accordingly, all such modifications are intended to be included within the scope of this invention as defined in the following claims, in accordance with relevant law as to their interpretation.

Nominal and Analyzed Compositions of Mg—Ca—Sr Alloys

TABLE 2

| | Mg (wt %) | | Ca (wt %) | | Sr (wt %) | |
|---|---|---|---|---|---|---|
| | Nominal | Analyzed | Nominal | Analyzed | Nominal | Analyzed |
| Mg—7.0Ca—3.5Sr | 90 | 89.13 | 7 | 7.32 | 3.5 | 3.55 |
| Mg—1.0Ca—2.0Sr | 97 | 96.93 | 1 | 1.18 | 2 | 1.89 |
| Mg—1.0Ca—1.0Sr | 98 | 97.99 | 1 | 1.21 | 1 | 0.80 |
| Mg—1.0Ca—0.5Sr | 98.5 | 98.24 | 1 | 1.29 | 0.5 | 0.47 |
| Mg—0.5Ca—0.5Sr | 99 | 98.96 | 0.5 | 0.55 | 0.5 | 0.49 |

EDS Analysis of the Phases in Mg-0.5Ca-0.5Sr Alloy

TABLE 3(a)

| | Mg (wt %) | Ca (wt %) | Sr (wt %) | O (wt %) |
|---|---|---|---|---|
| A | 72.2 | 3.1 | 23.5 | 1.2 |
| B | 92.6 | 4.1 | 1.5 | 1.8 |
| C | 98.6 | ≈0 | ≈0 | 1.4 |

EDS Analysis of the Phases in Mg-1.0Ca-0.5Sr Alloy

TABLE 3(b)

| | Mg (wt %) | Ca (wt %) | Sr (wt %) | O (wt %) |
|---|---|---|---|---|
| A | 70.83 | 13.50 | 12.23 | 3.44 |
| B | 82.86 | 9.60 | 2.22 | 5.31 |
| C | 98.64 | ≈0 | ≈0 | 1.36 |

EDS Analysis of the Phases in Mg-1.0Ca-1.0Sr Alloy

TABLE 3(c)

| | Mg (wt %) | Ca (wt %) | Sr (wt %) | O (wt %) |
|---|---|---|---|---|
| A | 71.74 | 7.55 | 19.70 | 1.01 |
| B | 86.15 | 7.97 | 4.56 | 1.32 |
| C | 99.07 | 0.48 | ≈0 | 0.45 |

Mechanical Properties of Alloy Samples.

TABLE 4

| Alloy Composition | Compressive Strength (MPa) |
|---|---|
| Mg—0.5Ca—0.5Sr | 274.3 ± 7.2 |
| Mg—1.0Ca—0.5Sr | 274.2 ± 4.0 |
| Mg—1.0Ca—1.0Sr | 214.5 ± 3.5 |

Mechanical Properties of Homogenized Mg—Sr

TABLE 5

| Alloy | 0.2% YS (MPa) | UTS (MPa) |
|---|---|---|
| Mg—0.5Sr | 37 | 74 |
| Mg—1.0Sr | 33 | 73 |
| Mg—1.5Sr | 40 | 81 |

What is claimed is:

1. A bioresorbable, non-toxic, osteogenic magnesium alloy, said alloy comprising, by weight percentage:
   1 percent calcium;
   0.5 percent strontium; and
   the remainder being magnesium; or said alloy comprising, by weight percentage:

0.3 percent calcium;
0.3 percent strontium; and
the remainder being magnesium.

2. A non-toxic, non-immunoreactive orthopedic implant comprised of the alloy of claim 1.

3. The implant of claim 2, wherein said alloy comprises at least 50 percent total weight of said implant.

4. The implant of claim 2 fashioned for insertion into a spine of a subject in need.

5. The implant of claim 4, wherein said implant is a cage, dowel or wedge.

6. The implant of claim 2, wherein said implant is a rod, screw, pin or plate.

7. A method of performing an orthopedic surgery, said surgery comprising inserting the implant of claim 2 into a subject in need.

8. An implant for use in orthopedic surgery, said implant comprising an alloy consisting essentially of magnesium, calcium and strontium; where the implant comprises by weight percentage:
   1 percent calcium;
   0.5 percent strontium; and
   the remainder being magnesium; or where the implant comprises by weight percentage:
   0.3 percent calcium;
   0.3 percent strontium; and
   the remainder being magnesium.

9. The alloy of claim 1, substantially free from aluminum, manganese, zirconium and/or zinc.

10. A dental implant comprised of the alloy of claim 1.

11. A method of orthopedic surgery which comprises surgically positioning the implant of claim 2 against a bone of a subject in need thereof.

12. The implant of claim 2, wherein said implant is a prosthetic femoral hip joint; a prosthetic femoral head; a prosthetic acetabular cup; a prosthetic elbow; a prosthetic knee; a prosthetic shoulder; a prosthetic wrist; a prosthetic ankle; a prosthetic hand; a prosthetic finger; a prosthetic toe; a prosthetic vertebrae; a prosthetic spinal disc; a prosthetic cochlea; a prosthetic vessel; or a prosthetic heart valve.

13. An alloy of claim 1, said alloy further comprising an osteogenic growth factor, hormone, nucleic acid sequence or drug.

14. The implant of claim 2, wherein said implant further comprises an osteogenic growth factor, hormone, nucleic acid sequence or drug.

* * * * *